United States Patent [19]

Solazzi

[11] 4,409,854
[45] Oct. 18, 1983

[54] SAMPLE CUP WITH VENTING MEANS FOR USE IN X-RAY SPECTROSCOPY

[75] Inventor: Michael C. Solazzi, Eastchester, N.Y.

[73] Assignee: Chemplex Industries, Inc., Eastchester, N.Y.

[21] Appl. No.: 317,533

[22] Filed: Nov. 2, 1981

[51] Int. Cl.³ .............................................. G01N 1/10
[52] U.S. Cl. ................................ 73/864.91; 356/246; 422/102; 250/428
[58] Field of Search ...................... 73/864.91; 422/102, 422/104; 356/246; 206/524.1, 628; 250/428

[56] References Cited

U.S. PATENT DOCUMENTS

| 3,378,684 | 4/1968 | Mentink et al. | 356/246 |
| 3,716,780 | 1/1973 | Shapiro | 422/102 |
| 4,037,109 | 7/1977 | Hosokawa | 356/246 |
| 4,346,299 | 8/1982 | Mitteldorf | 422/102 |

FOREIGN PATENT DOCUMENTS

| 135240 | 4/1979 | German Democratic Rep. | 73/864.91 |
| 664048 | 5/1979 | U.S.S.R. | 356/246 |

*Primary Examiner*—S. Clement Swisher

*Attorney, Agent, or Firm*—Arthur L. Plevy

[57] ABSTRACT

There is disclosed a sample cup for use in holding a sample for spectrochemical analysis. The sample cup consists of a cell member which is cup shaped and has a closed bottom and an opened top. The top surface of the closed bottom has a recessed section which extends towards the bottom surface at a given taper with the diameter being larger near the bottom surface of the closed bottom. This forms an area on the closed bottom which is relatively thin.

Located on the bottom surface of the closed bottom is an upstanding plunger which is positioned within the thin area. The plunger has grooves directed from top to bottom on the side walls and when depressed ruptures the closed bottom of the cell to create a vent necessary to equalize pressure. The sample cup is adapted to have its top opening covered by a thin plastic film which is secured in position by a collar and snap on ring assembly. The entire assembly with a sample is placed in a vacuum or gas environment and the plunger is depressed to rupture the closed bottom to provide pressure equalization when the cup is assembled as indicated.

10 Claims, 3 Drawing Figures

SAMPLE CUP WITH VENTING MEANS FOR USE IN X-RAY SPECTROSCOPY

BACKGROUND OF THE INVENTION

This invention relates to a sample cup for use in holding specimens for spectrochemical analysis and more particularly to such a cup including means for venting the same.

Sample cups for spectrochemical analysis are used in the prior art to hold or contains liquid, solids and powdered specimens under normal atmospheric pressures, gas pressures or in vacuum for analysis such as energy and wavelength dispersive techniques and optical emission methods. Such cups, as indicated, are in widespread use.

Essentially the sample cup consists of three components as a cup shaped cell having a closed bottom and an opened top, an annular collar and a snap on ring. A typical prior art cup is shown in U.S. Design Pat. No. 238,693 entitled CELL FOR X-RAY SPECTROSCOPY OR SIMILAR ARTICLE issued on Feb. 3, 1976 to Monte J. Solazzi.

The collar and the snap on ring serve to secure a sheet of plastic material such as mylar to cover the open top of the cell when the hollow of the cell is filled with a specimen as the liquid, solid or powdered material to be analyzed. Such cells are available from many sources such as Chemplex Industries, Inc., of 140 Marbledale Road, Eastchester, N.Y. 10707.

The cells of the prior art have a recessed or depressed small area on the closed bottom surface of the cell which can be punctured or pierced by means of a sharp point such as the tip of a ball-point pen or some other device. The pierced hole serves as a vent as will be explained and is used to equalize pressure within the sample cup.

For spectrochemical analytical investigation of specimens or analytes characterized with high abrogation properties in air, the entire assembled sample cup with the plastic sheet covering the top may be emplaced within a vacuum or an inert gas environment. Under conditions where pressure equalization is not implemented, the plastic sheet will distend or bow outwardly due to the vacuum or lower pressure. This then places the surface of the sheet closer to the excitation source which may be an X-ray tube or other device. The surface of the sheet of plastic is commonly defined as the sample plane. A variation in the distance from the sample plane to the source of excitation operates to alter the intensity of the characteristic radiation of the analyte and also the intensity of radiation impinging upon the sample from the excitation source. The variations result in erroneous quantitative data and hence cannot be tolerated. As indicated for applications in a vacuum environment the thin plastic film distends or bows out (convex) which decreases the distance from the sample to the excitation source. For applications in a gaseous environment (positive pressure) the thin plastic film tends to be drawn into the hollow of the cell or provides a concave surface. This effect increases the distance between the sample plane and the excitation source resulting in lower values of analytical data.

In order to equalize the pressure the prior art had a section in the closed bottom surface of the cell which allowed one to pierce a hole in the cup or vent the cup. In any event the technique relied on the skill of the operator and if too much force were employed the hole would be too large, the sample might become contaminated or the parts of the cup dislodged.

Thus the prior art technique is not a convenient way of providing venting of sample cups.

It is therefore an object of the present invention to provide an improved sample cup including venting means which enable an operator to provide venting in a rapid and precise manner.

DESCRIPTION OF THE PREFERRED EMBODIMENT

A sample cup for retaining a specimen to be subjected to spectrochemical analysis constitutes a cell section which is a cup shaped member having a closed bottom and an opened top. The top surface of said closed bottom has a recessed section of a greater diameter near the bottom surface of the closed bottom. The recessed section tapers to a smaller diameter facing the opened top. The thickness of material located below the recessed section is relatively thin. Located on the bottom surface of the closed bottom and below the recessed area is an extending plunger which when pushed towards the opened top ruptures the thin portion of the bottom surface. The tapered recess operates to capture the plunger and hence to prevent the plunger from falling into the sample containing hollow of the cell.

DETAILED DESCRIPTION OF THE INVENTION

Figure 1:
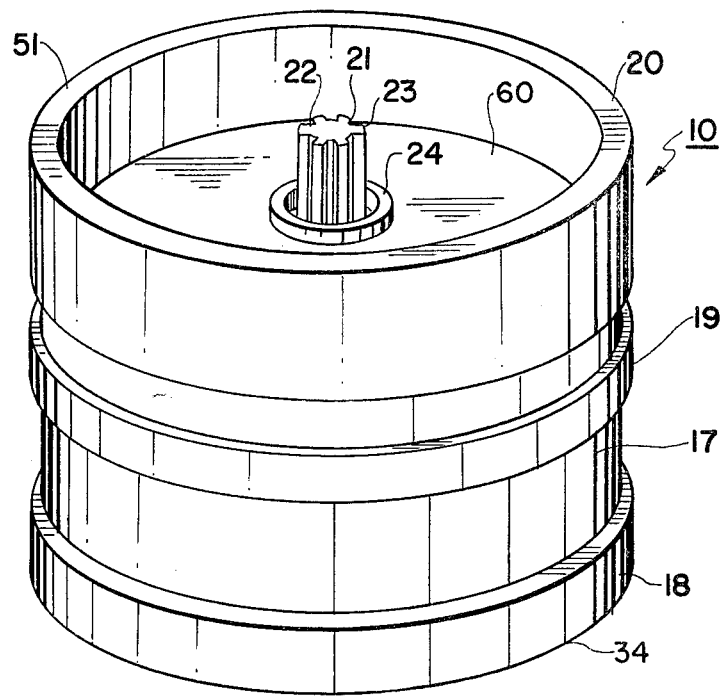
FIG. 1 is a perspective plan view of a sample cup according to this invention.

Referring to FIG. 1, there is shown a sample cup 10. The cup 10 is shown with the bottom surface 60 of the closed bottom 35 facing upward. As will be explained, the cup has an opened top 34 and is generally cylindrical in shape. The sample cup consists essentially of three components. There is a main cell component 17 which is essentially a cup like member having an opened top 16 and a closed bottom 35. There is shown an annular member or ring 18 which is a collar and is used to retain a thin plastic film over the opened top after a sample has been introduced into the hollow confines of the cell 17. Also shown is an annular ring 19 which is a snap on ring and is used together with collar 18 in holding the plastic film in the secure position. The bottom of the cell 17 has an extending peripheral flange 20 which flange encircles the bottom surface 60 of the closed bottom 35.

Shown in FIG. 1 is an extending post or plunger 21. The plunger 21 is a cylindrical member and essentially has a series of grooves or slots which are directed from the top to the bottom of the member 21. The plunger member 21 is integrally formed above a recessed portion or aperture which is located on the top surface of the closed bottom 35 as will be described. Surrounding the plunger member 21 is a peripheral flange 24 which is used to provide support, as will be explained. Essentially the recess and the plunger member 21 are indicative of unique features of this sample cup as compared to those of the prior art.

Figure 2:
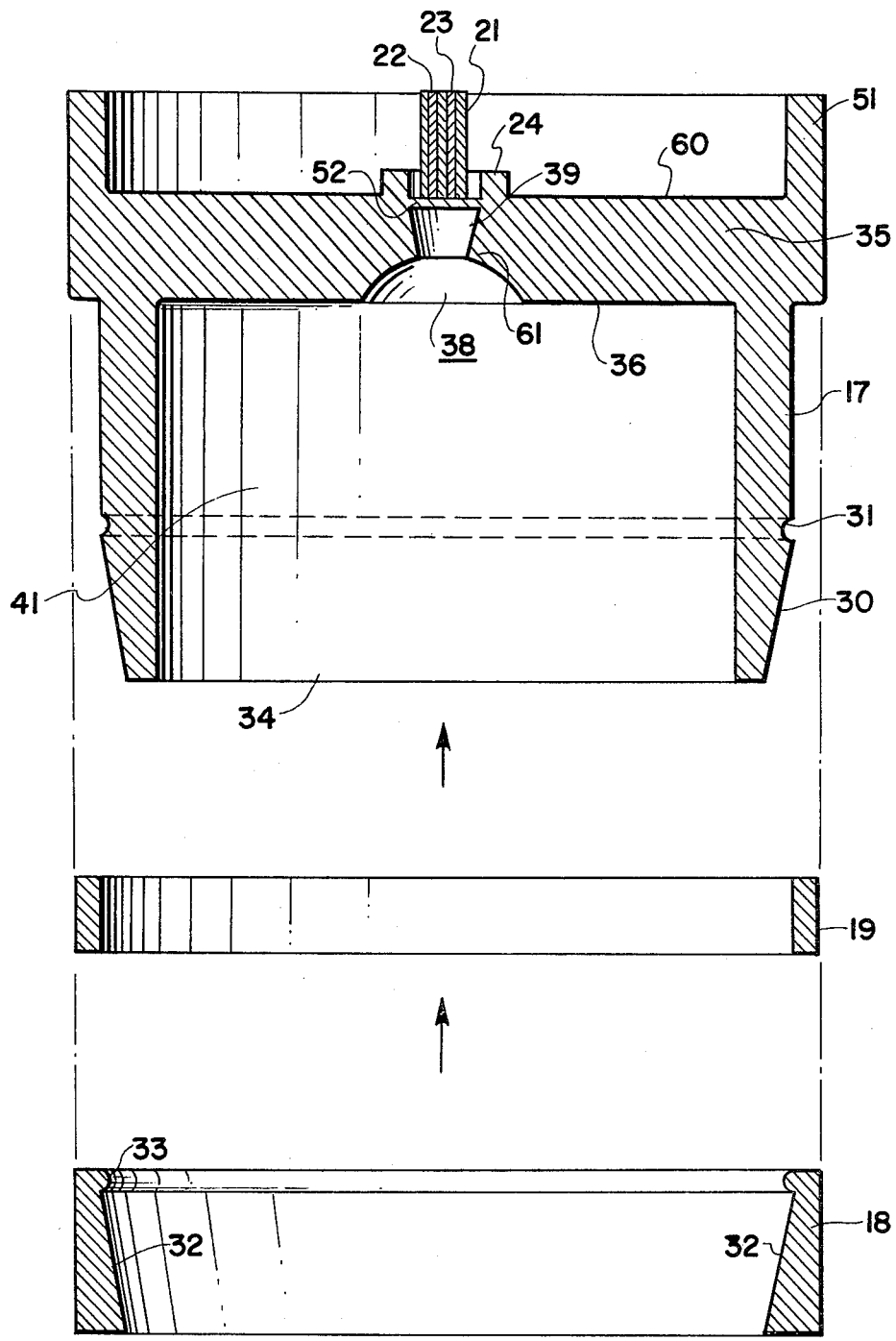
FIG. 2 is an assembly view in cross-section of the components constituting a sample cup.

Referring to FIG. 2, there is shown a cross-sectional view of the sample cup 10 clearly depicting the cell 17, the snap on ring 19 and the collar 18. Referring to FIG. 2, the cell is generally cylindrical in structure and is fabricated from a suitable plastic such as polypropylene. Polypropylene and other plastics as well, offer rigidity and have resistance to chemical attack. Thus these plastics are particularly useful in providing sample cup structures. The cell 17 has a tapered portion 30 about the top surface thereof with a circumferential groove 31. The taper 30 and groove 31 are adapted to coact with and retain the collar member 18 in position. As can be seen, the collar member 18 has tapered sides 32 which corresponds to the side 30 of the cell 17. There is also an extending circular projection or flange 33 which fits into groove 31 to thereby hold the collar 18 in place on the cell portion 17.

The cell portion or section 17 has an opened top 34 and a closed top 35. The bottom surface 36 of the closed bottom 35 has a recessed portion or section 38. As can be seen from FIG. 2, the recessed portion 38 has a first semi-spherical aperture which is contiguous with a tapered portion 39. The tapered portion 39 has a large diameter near the bottom surface 60 of the closed bottom 35 and then tapers to a smaller diameter at point 61 where it interfaces with the semi-spherical recessed portion 38.

As can be seen, there is a small thickness of material defining an area 52 where the thickness of the closed bottom 35 is relatively thin. Located within area 52 is the plunger member or post 21 having the grooves 22 and 23 extending from the top to bottom. The member 21 is cylindrical and has a cross-section of a gear like appearance due to the grooves or slots in the side surface. Surrounding member 21 is the extending flange 24. As can be seen from FIG. 2, the plunger 21 is of a smaller diameter than the inner diameter of the flange 24 and a small amount of material in area 52 is included between the inner diameter of the flange 24 and the side walls of the plunger member 21.

Figure 3:
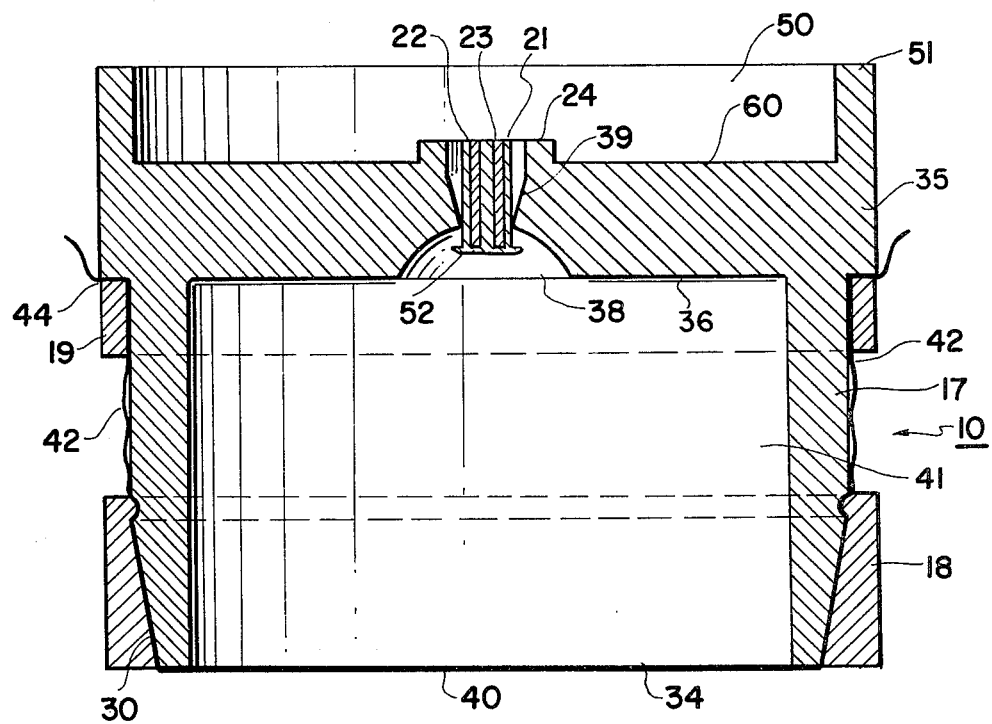
FIG. 3 is a cross-sectional view of an assembled sample cup showing an activated venting condition.

Referring to FIG. 3, there is shown a cross-sectional view of the sample cup 10 accomodating a thin plastic film 40 which may be fabricated from a polyester, polypropylene or a polycarbonate. In order to use the cup 10 a sample of material is introduced into the hollow 41 of the cell 17. To do this the cell is inverted from the position shown in FIGS. 2 and 3 and thus the opened top 34 of cell 17 is facing upward. The sample as introduced fills the hollow 41 to the top edge of the cell. A thin plastic film 40 is then placed over the opening 34 with the side edges 42 of the film directed about the sides of the cell. The collar 18 is then used to affix the film 40 in a temporary position by pushing the collar 18 down until it abuts up to the flared or tapered end of the cell. The snap on ring 19 is then placed over the aperture of the cell and over the temporary collar held thin film and is pushed down until it locks in position by abutting against the edge 44 of the cell 17. The interior ridge of the ring 19 in conjunction with the tapered neck 30 of the cell 17 firmly grasps the film 40 during assembly to create and maintain a taut, wrinkle free sample plane as the ring 19 is pushed down. The peripheral groove 31 on the cell neck and the matching projection 33 of the collar 18 serve to retain the thin film sample plane in position after assembly.

As explained above, in order to maintain equalization of pressure and to maintain a taut, thin film plane, the cell 17 includes the grooved plunger 21 which is located as shown in FIG. 2 on the bottom surface 60 of the closed bottom 35.

As indicated in FIG. 2, the plunger 21 is integrally formed with the bottom surface 60 of the closed bottom 35 and provides a seal as shown in FIG. 2. In practice, the assembled cell or sample cup 10 in FIG. 3 is then positioned as shown so that the thin film sample plane 40 is facing downward. The plunger 21 is then pushed downwardly in order to rupture the seal and creates an opening in the bottom surface 35. This creates a venting passageway communicating with the internal hollow 41 of the cell.

As seen in FIG. 3, the tapered aperture of the recessed section 38 prevents the plunger 29 from falling into the hollow 41. The extending flange 24 prevents a user from pushing the plunger to great a distance and acts as a stop to prevent the plunger 21 from being over depressed. Thus as can be seen from FIG. 3, when the cup is operated in a vacuum or gaseous environment, the plunger when rupturing the bottom surface will establish an equalization of pressure. The grooves as 22 and 23 which are arranged about the periphery of the plunger 21, permit pathways from the interior of the cell to the exterior environment by preventing a false seal which may possibly be created between the constricted radius or tapered portion 39 and the wall of the plunger 21.

therefore, the grooves assure that a continuous path will be formed which enables the internal hollow 41 to communicate with the outside environment when the plunger 21 is pushed to rupture the bottom surface.

As also shown in FIG. 3, upon rupture of the seal a small thin section of material from area 52 remains attached to the bottom of the depressed plunger. This material forms a thin peripheral rim about the bottom of the plunger. This rim serves as a deflector for preventing the potential escape of any agitated powdered sample particles or solution droplets which may otherwise escape during the initial stage of establishing the vacuum or gas pressure equalization. In operation as depicted in FIG. 3, the venting procedure as implemented by the plunger 21 serves to overcome distension of the thin film sample plane 40.

Furthermore, if sample material does pass through the grooves in the plunger 21, it will be included in the space 50 and prevented from spilling due to the outer peripheral flange 51 which extends upwardly from the top surface 60 of the closed bottom.

For spectrochemical applications which do not require a vacuum or a gas environment, as well as samples susceptible to outgasing, volatility or thermal degradation, the venting procedure also serves to overcome distension of the thin film sample plane 40 which may be caused by radiation or heat generation and hence one may desire to vent the sample cup by depressing the plunger 21 during these additional operations.

I claim:

1. A sample cup for retaining a specimen to be subjected to spectrochemical analysis, comprising:
a cup shaped member (10) having a closed bottom (35) and an opened top (34), with the top surface (36) of said closed bottom (35) of said member (10) having a recessed section (39) of a first diameter nearer the bottom surface (60) of said closed bottom (35) and tapering to a smaller diameter then said first, facing and in direct communication with said opened top (34), whereby the thickness of said closed bottom (35) at said recessed section (52) is relatively thin, a plunger (21) extending transversely from the bottom surface (60) of said closed bottom (35) and located below said recess, whereby when said plunger is pushed towards said opened top said thin portion of said closed bottom is ruptured with the sides of said plunger being captured within said recessed portion to prevent the plunger from falling through said top opening.

2. The sample cup according to claim 1 further including a thin plastic film covering said opened top of said cup shaped member and having side edges extending over the outer surface of said cup shaped member, and means coupling said side edges of said film to said cup shaped member for securing said film in position.

3. The sample cup according to claim 1 wherein said plunger has a series of grooves located on the side surface thereof and extending from the top to the bottom.

4. The sample cup according to claim 1 wherein said plunger is surrounded by an extending circular flange secured to the bottom surface of said closed botton.

5. The sample cup according to claim 1 wherein said recessed portion further has a larger circular depression contiguous with the smaller diameter portion of said recessed section nearest said opened top.

6. The sample cup according to claim 1 wherein said cup is a cylindrical member as is said plunger.

7. The sample cup according to claim 1 wherein said plunger is of a smaller diameter then said diameter of said recessed section near said top surface of said closed bottom to cause said plunger when pushed downwardly to include a peripheral rim formed by additional material within said thin recessed section.

8. The sample cup according to claim 2 wherein said means coupling said thin film to said cup shaped member is an annular band adapted to encircle the sides of said cup shaped member to secure said film in position.

9. The sample cup according to claim 1 wherein the bottom of said closed bottom surface further includes continuous extending peripheral flange located about the outer edge of said closed surface.

10. The sample cup according to claim 1 wherein said cup shaped member is fabricated from polypropylene.

* * * * *